United States Patent [19]
Goel et al.

[11] Patent Number: 4,655,974
[45] Date of Patent: * Apr. 7, 1987

[54] MANUFACTURE OF PHENYL ESTERS

[76] Inventors: Anil B. Goel, 373 Eastworth Ct., Worthington, Ohio 43085; Robert A. Grimm, 1810 Ivanhoe Ct., Columbus, Ohio 43220

[*] Notice: The portion of the term of this patent subsequent to Aug. 7, 2001 has been disclaimed.

[21] Appl. No.: 717,713

[22] Filed: Apr. 4, 1984

Related U.S. Application Data

[63] Continuation-in-part of Ser. No. 348,561, Feb. 2, 1982.

[51] Int. Cl.$^4$ .................. C07C 67/00; C09F 5/08; C09F 7/10
[52] U.S. Cl. .................. 260/410; 260/410.5; 560/131
[58] Field of Search .................. 260/410.5, 410.0 R; 560/131

[56] References Cited

U.S. PATENT DOCUMENTS

| | | | |
|---|---|---|---|
| 3,493,605 | 2/1970 | Selwitz | 260/488 |
| 3,646,111 | 2/1972 | Hörnig et al. | 560/131 |
| 3,772,383 | 11/1973 | Kominami et al. | 560/131 |
| 4,229,587 | 10/1980 | Murib | 560/131 |
| 4,464,303 | 8/1984 | Goel | 260/410 |
| 4,508,653 | 4/1985 | Goel | 260/410.5 |

Primary Examiner—Charles F. Warren
Assistant Examiner—Elizabeth A. Flaherty
Attorney, Agent, or Firm—John F. Jones

[57] ABSTRACT

A process is described for the manufacture of aryl esters such as phenyl esters by liquid phase reaction of an aromatic compound such as benzene with molecular oxygen in the presence of a carboxylic acid preferably having 6 or more carbon atoms over a catalyst composed essentially of a compound of palladium and an antimony compound wherein the aromatic compound is added continuously to the reaction and water formed in the reaction is rapidly and continuously removed from the reaction zone.

8 Claims, No Drawings

MANUFACTURE OF PHENYL ESTERS

This is a continuation in part of our copending patent application Ser. No. 348,561, filed Feb. 2, 1982.

BACKGROUND OF THE INVENTION

1. Field of the Invention

The present invention provides a process for making phenolic esters and if desired, phenols from aromatic compounds such as benzene, naphthalene, anthracene, biphenyl, etc. which comprises reacting a mixture of the aromatic compound, for instance benzene, a carboxylic acid, preferably having at least 6 carbon atoms, and molecular oxygen in the liquid phase in the presence of a catalyst consisting essentially of palladium or a compound of palladium and a compound of antimony.

2. Description of the Prior Art

The manufacture of phenol by direct oxidation of benzene with oxygen is known. There are, for instance, thermal processes which are performed at very high temperatures in which the phenol formed is susceptible to further oxidation so that considerable loss of yield occurs as is disclosed in U.S. Pat. No. 2,223,383. In the presence of catalysts, the oxidation can be carried out at somewhat lower temperatures as in U S. Pat. No. 3,133,122 but the reactions have been plagued by low conversions and excessive production of unwanted by-products as disclosed in U.S. Pat. No. 2,392,875.

It has already been proposed to make phenyl acetate and biphenyl from benzene and acetic acid in the liquid phase in the presence of palladium acetate and without added molecular oxygen by a stoichiometric reaction in *CHEM AND IND.*, Mar. 12, 1966, page 457.

U.S. Pat. No. 3,542,852 discloses the preparation of hydroxy aromatic compounds by reaction of an aromatic compound and oxygen in the presence of a catalyst composed of iron, a noble metal or a compound of either in the presence of a nitrate ion and a carboxylic acid. More recently the preparation of phenyl esters and phenols by the reaction of benzene, molecular oxygen and a lower aliphatic carboxylic acid in the presence of a catalyst composed of a Group VIII metal (U.S. Pat. No. 3,642,873) or a compound of such metal (U.S. Pat. No. 3,651,127) have been disclosed. Similarly, variations in this type of reaction have been disclosed in U.S. Pat. Nos. 3,646,111; 3,651,101; 3,772,383; 3,959,352 and 3,959,354. U.S. Pat. No. 3,959,354 concludes that liquid phase reactions of this type because of problems of catalyst elution, etc. are disadvantageous for an industrial process. U.S. Pat. No. 3,772,383 describes a liquid phase reaction using a very complex catalyst system which includes the use of nitric acid and a lower aliphatic carboxylic acid such as acetic, propionic, n-butyric, isobutyric or caproic acid. Generally speaking, these prior art processes deal for the most part with vapor phase oxidation reactions, or liquid phase reactions in which all the reactants (except oxygen in some instances) are initially included in the reaction mixture, they use lower aliphatic carboxylic acids such as acetic acid and propionic acid, and they often require an alkali or alkaline earth metal carboxylate as part of the catalyst. Moreover, in general the prior art catalytic processes have produced very low conversions, usually less than 10%, with poor selectivity to the desired phenyl ester, and phenol is often a primary product. The use of the lower saturated carboxylic acids, primarily acetic acid, in the prior art processes produce a highly corrosive system which can cause reaction equipment problems and excessive recycle costs as well as the poor conversions and selectivities mentioned above. None of the prior art processes disclose the continuous addition and removal of benzene and continuous removal of water from the reaction mixture as it forms.

SUMMARY OF THE INVENTION

We have discovered an oxidation process for the transformation of benzene, and similar aromatic compounds, molecular oxygen and a carboxylic acid to the corresponding aromatic carboxylate in high conversions and selectivities to the desired product Our discovery is based to some extent upon the use of relatively higher boiling mono or poly-carboxylic acid such as lauric acid or dodecanedioic acid as the carboxylic acid reactant in our process. We have discovered that the use of carboxylic acids having 6 or more carbon atoms and a liquid reaction phase in our process as well as our palladium-antimony catalyst not only helps in dramatically increasing the conversion of benzene and increasing the selectivity to the phenyl carboxylate over that described in the prior art, but that these carboxylic acids are much less corrosive and much easier to recycle than are the lower aliphatic carboxylic acids disclosed for similar types of reactions in the prior art.

We have also discovered in contrast to what was previously known in the art that our liquid phase reaction produces high conversions and quantitative yields of phenyl ester when benzene is continuously added to and removed from the reaction mixture during the entire course of the reaction. Excess amounts of benzene in the reaction mixture during the oxidation reaction appear to be responsible for production of undesirable by-products such as biphenyl Benzene removal is employed primarily because it entrains and removes water from the reaction mixture as water is formed in the reaction. If water, which is a by-product of the oxidation reaction, is allowed to remain in the reaction mixture it causes hydrolysis of the phenylester to phenol which can cause fouling of catalyst.

The catalysts of our process are preferably composed of palladium metal or compounds of palladium and usually a palladium carboxylate for convenience in conjunction with an antimony compound and usually an antimony carboxylate also convenience. The use of significant amounts of other materials such as those described as being catalyst promoters in the prior art in addition to the essential palladium and antimony components of our catalyst is usually detrimental to our process. The catalysts of this invention may be used alone or may be supported on a carrier or carriers. Suitable carriers include silica, alumina, carbon, quartz, pumice, diatomaceous earth, and the like and others which are well known in the art.

The carboxylic acids useful in our invention include mono and poly-carboxylic acids and preferably those having 6 or more carbon atoms and some carboxylic acid anhydride can be included with the carboxylic acid if desired.

Our liquid phase oxidation process produces in the case of benzene reactant conversions of the carboxylic acid in the order of 10% or greater with selectivities to the phenyl ester in the order of 100%. Thus, our process produces product in such significant quantities that it is directly competitive with the best of the present day commercial processes for the manufacture of phenyl esters and ultimately phenol itself. The phenyl ester or phenyl carboxylate product of our process can readily be converted to phenol and the corresponding carboxylic acid by known methods for hydrolysis or pyrolysis. The phenol is easily recovered by known means and the carboxylic acid, ketene or acid anhydride is readily recycled for further use in the oxidation reaction of this invention.

DESCRIPTION OF THE PREFERRED EMBODIMENT

In a typical reaction in accordance with this invention a mixture of benzene and the carboxylic acid is contacted with a catalyst in an oxygen containing atmosphere at a reaction temperature in the range of from about 100° to 300° C. and preferred from 140°–200° C. and at from 1 to 100, preferably 1 to 10 atmospheres but more preferably at or near atmospheric pressure. The molecular oxygen can be oxygen per se, or any gaseous mixture containing molecular oxygen. For instance, molecular oxygen can be in the form of air for convenience. The catalyst can be a mixture of $(CH_3COO)_2Pd$ and $(CH_3COO)_3Sb$, for instance, in molar ratio of about 1:1. This molar ratio of Pd:Sb can vary within the range of from 1:0.01 to 1:20 and preferably 1:0.1 to 1:10. During the reaction usually the liquid reaction mixture slowly turns dark brown and the water formed is continuously removed conveniently by azeotropic distillation with benzene which is continuously added to the reactor. The major product (and in most cases the only product), the phenyl carboxylate obtained by the process of this invention, far exceeds the best yields reported in the prior art with essentially quantitative selectivity. As previously mentioned, the phenyl carboxylate thus obtained can be hydrolyzed if so desired to produce phenol by known means and the carboxylic acid and catalyst can be recycled back into the oxidation reaction.

Because essentially no phenol is produced in the process of this invention, it is believed that catalyst activity is maintained for long periods of time under continuous use. The rapid removal of water from the reaction mixture is probably at least partly responsible for the absence of phenol in the reaction product. The presence of phenol in the reactor is believed to be responsible for catalyst fouling and short catalyst life. The process of this invention is further demonstrated in the following illustrative examples.

EXAMPLE I

To a stirred reactor were added 127 g. (552 millimols) of dodecanedioic acid, 2.7 g. (12 millimols) of $Pd(OAc)_2$ 8.47 g. (24 millimols) of $Ph_3Sb$, and 8 ml. (6.89 g. or 88 millimols) of benzene. The brown colored solution reaction mixture was stirred continuously, maintained at 165° C. and oxygen was bubbled through the reaction liquid at a flow rate of about 50 cc. per minute. Water formed during the reaction and was removed continuously as it formed azeotropically with excess benzene. The reaction temperature was maintained within 5° C. plus or minus from 165° C. during the course of the reaction and additional benzene was fed to the reactor by pump. The reaction was carried out for 5 hours during which time 2.9 ml. (162 millimols) of water was produced and the total benzene fed was 21.0 g. (269 millimols). GLC analysis of the reaction mixture after the 5 hour reaction time showed that 60% of the benzene was converted with a 98% selectivity to the phenyl ester of dodecanedioic acid.

EXAMPLE 2

To a 500 ml. 3 neck flask equipped with a mechanical stirrer, reflux condenser and Dean Stark (drying) tube, was charged 2,7 g. of palladium (II) acetate (0.012 mol), 3.6 g. antimony (III) acetate (0.012 mol), 127 g. (0.552 mol) of dodecanedioic acid and 10 ml. of benzene. The resulting mixture was stirred and heated to 165° C. and oxygen was bubbled through the reaction liquid at a flow rate of about 50 cc./minute. Water formed during the reaction and was removed continuously as it formed azeotropically with excess benzene. The reaction temperature was maintained at 165° C.±3° C. during the course of the reaction and additional benzene was fed to the reactor by pump. The reaction was carried out for 5.5 hours during which time about 4 ml. (222 millimols) of water was produced and the total benzene fed was 0.459 mols. GLC analysis of the reaction mixture after 5.5 hours reaction time showed the formation of the phenyl ester of dodecanedioic acid (188 millimols; 34% conversion of the dodecanedioic acid) with 100% selectivity to the phenyl ester. About 4 millimols of the diphenyl ester of dodecanedioic acid were observed but no biphenyl or phenol were detected.

EXAMPLE 3

The procedure of Example 2 was repeated in a 250 ml. flask and the reagents charged were $Pd(OAc)_2$ (1.35 g.; 0.006 mol), $Sb_2O_3$ (1.77 g., 0.006 mol), dodecanedioic acid (63.5 g.; 0.276 mol), and benzene (5 ml.). Total benzene fed during the reaction time of 5 hours was 0.182 mol. Analysis showed that about 15% of the dodecanedioic acid was converted to produce 35 millimols of the phenyl ester of dodecanedioic acid with 100% selectivity.

EXAMPLE 4

The procedure of Example 3 was followed except that 0.277 mol of lauric acid was used in place of dodecanedioic acid and 0.006 mol of antimony (III) acetate was used instead of $Sb_2O_3$. During 6 hours of reaction at 160° C.±3° C. about 0.19 mol of benzene was introduced into the reaction mixture. Analysis showed that 10% of the lauric acid was converted to the phenyl ester of lauric acid (28 millimols) with near 100% selectivity.

EXAMPLE 5

The procedure of Example 4 was followed except that 0.276 mol of adipic acid was used in place of the lauric acid. The reaction was carried out for 5 hours at 162°±3° C. Analysis showed that about 16% of the adipic acid was converted to phenyl ester (45 millimols) with 100% selectivity.

EXAMPLE 6

The procedure of Example 5 was repeated except that 0.284 of isobutyric acid was used instead of adipic acid. The reaction was carried out for 2.5 hours at 150°–155° C. and the total benzene fed was 0.37 mol. Analysis showed that 3% of the isobutyric acid (11 millimols) was converted to the phenyl ester with 100% selectivity.

EXAMPLE 7

The procedure of Example 4 was repeated except that 0.874 mol of acetic acid was used in place of the lauric acid. The reaction was carried out at about 85° C.

for 3 hours. Analysis showed that only a trace amount of phenyl acetate formed and 8 millimols of biphenyl were formed.

EXAMPLE 8

The procedure of Example 4 was repeated except that 0.006 mol of copper(II)acetate was used in place of the $Sb_2O_3$. The reaction was carried out at 168° C. for 5 hours during which time 0.18 mol of benzene was fed. Analysis showed that 7% of the dodecanedioic acid was converted to phenyl ester (19 millimols) with 100% selectivity.

EXAMPLE 9

The procedure of Example 8 was repeated except that 0.006 mol of $Tl(OAc)_3$ was charged instead of copper acetate. The reaction was carried out at 165° C.±5° C. for 5 hours and 0.23 mol of benzene was fed. Analysis showed that 2.5% of the dodecanedioic acid was converted to phenyl ester (7 millimols) with about 90% selectivity.

EXAMPLE 10

The procedure of Example 9 was repeated except that 0.006 millimols of $TeO_2$ was used in place of the $Tl(OAc)_3$. Analysis showed that 2% of the dodecanedioic acid was converted to phenyl ester (5 millimols) with 90% selectivity.

EXAMPLE 11

The procedure of Example 3 was followed except that $Sb(OAc)_3$ was used in place of the $Sb_2O_3$ and the potassium salt of dodecanedioic acid was included. In the reaction mixture there were included 0.276 mol of dodecanedioic acid, 0.006 mol of $Pd(OAc)_2$, 0.006 mol of $Sb(OAc)_3$ and 0.012 mol of the mono-potassium salt of dodecanedioic acid. The reaction was carried out at 165° C. for 7 hours during which time 0.187 mol of benzene was introduced. Analysis showed that about 10% of the dodecanedioic acid was converted to phenyl ester (27 millimols) with about 99% selectivity.

EXAMPLE 12

The procedure of Example 11 was followed except that lauric acid was used in place of dodecanedioic acid and .0.012 mol of the potassium salt of lauric acid was used in place of the potassium salt of dodecanedioic acid. After 7 hours of reaction about 4% of the lauric acid was found to be converted to the phenyl ester (10 millimols) with about 95% selectivity.

EXAMPLE 13

The procedure of Example 4 was repeated except that 0.276 mol of dodecanedioic acid was used instead of lauric acid. The reaction was carried out for 5 hours during which time 0.2 mol of benzene was fed. Analysis showed that 24% of the dodecanedioic acid was converted to give 66 millimols of the phenyl ester of dodecanedioic acid with 100% selectivity.

EXAMPLE 14

The procedure of Example 13 was repeated except that 0.006 mol of zinc acetate was included in the charge. After reaction for 5 hours, analysis showed that less than 2% dodecanedioic acid was converted to give the phenyl ester of dodecanedioic acid (5 millimols).

EXAMPLE 15

The procedure of Example 14 was repeated except that 0.006 mol of lead acetate was used instead of the zinc acetate. At the end of the reaction time analysis showed that less than 3% of the dodecanedioic acid was converted to the phenyl ester (7 millimols).

EXAMPLE 16

The procedure of Example 3 was repeated except that the amounts of $Pd(OAc)_2$ and $Sb(OAc)_3$ (in place of $Sb_2Ohd\ 3$ used were 0.009 mol each. Analysis at the end of the reaction time showed that 41% of the dodecanedioic acid was converted to the monophenyl ester (112 millimols) and diphenyl ester (6 millimols) with 100% selectivity.

EXAMPLE 17

The reaction was carried out in a closed reactor which was a 5 ml. mini reactor, equipped with a screw cap containing a Teflon liner. The reactor was charged with 0.5 g. of dodecanedioic acid 0.5 ml. of benzene, 0.2 g. of $Pd(OAc)_2$, 0.3 g. of $Sb(OAc)_3$ and filled with oxygen and closed. The reaction was carried out at 170°±5° C. for 5 hours during which the color of the reaction mixture turned brownish-black. Analysis showed that phenol, phenyl acetate, biphenyl and the phenyl ester of dodecanedioic acid were present in the reaction mixture in the weight ratios of 5:10:75:10, respectively.

EXAMPLE 18

The procedure of Example 17 was repeated except that propionic acid was used in place of the dodecanedioic acid. After the designated reaction time analysis showed the formation of phenyl acetate, phenyl propionate and biphenyl in the weight percent ratios 18:35:47, respectively.

EXAMPLE 19

The procedure of Example 16 was repeated except that 0.018 mol each of $Pd(OAc)_2$ and $Sb(OAc)_3$ were used. The reaction was carried out at 166°±2° C. for 5 hours. Analysis showed 24% conversion of dodecanedioic acid to give 72 millimols of the phenyl ester.

EXAMPLE 20

This Example describes one method for hydrolysis of the phenyl ester of dodecanedioic acid prepared as in Example 1,3. 20 g. of the reaction mixture containing 24% by weight of phenyl ester of dodecanedioic acid was extracted with 250 ml. of diethyl ether after stirring for about 30 minutes. The ether extract was heated to volatilize the ether and remove it and the residual material was mixed with 100 ml. of water and treated with 1.52 N KOH and heated on a steam bath for about two hours. A clear solution resulted. The pH of this solution was adjusted to about 4.0 and the insoluble solid (mainly dodecanedioic acid) was removed by filtration and the filtrate was extracted with diethyl ether (2-200 ml. portions), dried over anhydrous $MgSO_4$ and ether removed to give about 1.1 g. (98% selectivity) of phenol.

EXAMPLE 21

This Example shows another hydrolysis method for obtaining phenol from the phenyl ester-catalyst reaction mixture. To a reaction mixture (75 g.) obtained by the procedure of Example 13 which contained 24% by weight of phenyl ester, unreacted dodecanedioic acid and the Pd(OAc)$_2$ Sb(OAc)$_3$ catalyst was added 250 ml. of water. This mixture was refluxed for 5 hours. After cooling, the reaction mixture was filtered to remove solid materials. The filtrate was extracted with ether and about 90% of the theoretical amount of phenol was recovered from the ether extract.

EXAMPLE 22

This Example describes a catalyst recycle procedure. The insoluble solid material which was removed by filtration from the hydrolysis step which was primarily catalyst and dodecanedioic acid was dried under reduced pressure. The resulting dried solid was transferred to a reactor and the procedure described in Example 13 was repeated using this recycled catalyst and dodecanedioic acid along with benzene and oxygen. Analysis showed that about 20% of the dodecanedioic acid was converted to produce 50 millimols of phenyl ester with essentially 100% selectivity.

EXAMPLE 23

In order to study the catalyst life in the oxidation reaction of this invention the procedure of Example 4 was followed except that it was continuous for 27 hours. Benzene and oxygen were fed continuously during the course of this reaction and three additional 0.05 mol portions of lauric acid were charged to the reaction mixture after 6, 14 and 20.5 hours on stream. The phenyl ester of lauric acid was formed exclusively during the entire reaction. Analysis performed on samples of the reaction mixture at the end of 6, 14, 20.5 and 27 hours on stream showed the formation of 13.3, 26, 34 and 39 millimols of phenyl ester, respectively. No biphenyl was observed even after 27 hours on stream and this Example shows that the catalyst retains its life over long periods of time with no evidence of decay. What might appear to be a slow decrease in product formation is actually a simple dilution effect due to the incremental addition of lauric acid described above.

EXAMPLE 24

The procedure of Example 4 was followed except that benzoic acid (0.33 mol) was used instead of lauric acid. The reaction was carried out under the conditions of Example 4 and 0.14 mol of benzene was fed. Analysis of the reaction mixture at the end of the reaction showed that 35 millimols (11% conversion of benzoic acid) of phenyl benzoate were produced.

We Claim:

1. An oxidation process for the manufacture of phenyl esters consisting essentially of contacting a reaction mixture of benzene, a mono or poly-carboxylic acid having 6 or more carbon atoms and molecular oxygen in the liquid phase at a temperature in the range of 100° to 300° C. with a catalyst consisting of a palladium carboxylate and an antimony carboxylate wherein the benzene is added continuously to the reaction mixture and the water formed in the process is removed continuously from the reaction mixture as the phenyl ester is formed.

2. The process of claim 1 wherein the palladium compound is palladium acetate.

3. The process of claim 2 wherein the antimony compound is antimony acetate.

4. The process of claim 3 wherein the carboxylic acid is dodecanedioic acid.

5. The process of claim 3 wherein the carboxylic acid is lauric acid.

6. The process of claim 3 wherein the carboxylic acid is adipic acid.

7. The process of claim 1 wherein the phenyl ester product is further hydrolyzed to form phenol and the phenol is recovered.

8. The process of claim 7 wherein the catalyst and carboxylic acid are recovered and recycled to the oxidation process step.

* * * * *